(12) United States Patent
Gerland

(10) Patent No.: US 9,295,432 B2
(45) Date of Patent: Mar. 29, 2016

(54) METHOD OF DETERMINING DISTRIBUTION OF A DOSE IN A BODY

(71) Applicant: KONINKLIJKE PHILIPS N.V., Eindhoven (NL)

(72) Inventor: Elazar Lars Gerland, Haifa (IL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/434,410

(22) PCT Filed: Oct. 10, 2013

(86) PCT No.: PCT/IB2013/059266
§ 371 (c)(1),
(2) Date: Apr. 9, 2015

(87) PCT Pub. No.: WO2014/060913
PCT Pub. Date: Apr. 24, 2014

(65) Prior Publication Data
US 2015/0265224 A1 Sep. 24, 2015

Related U.S. Application Data

(60) Provisional application No. 61/715,930, filed on Oct. 19, 2010, provisional application No. 61/716,843, filed on Oct. 22, 2012.

(51) Int. Cl.
*G06K 9/00* (2006.01)
*A61B 6/03* (2006.01)
*A61B 6/00* (2006.01)
*G06T 7/00* (2006.01)

(52) U.S. Cl.
CPC .......... *A61B 6/032* (2013.01); *A61B 6/037* (2013.01); *A61B 6/466* (2013.01); *A61B 6/5217* (2013.01); *A61B 6/5294* (2013.01); *A61B 6/542* (2013.01); *G06T 7/0012* (2013.01); *G06T 2207/10028* (2013.01); *G06T 2207/10081* (2013.01); *G06T 2207/10104* (2013.01); *G06T 2207/20104* (2013.01)

(58) Field of Classification Search
None
See application file for complete search history.

(56) References Cited

U.S. PATENT DOCUMENTS

| 7,627,079 | B2 | 12/2009 | Boone | |
|---|---|---|---|---|
| 2008/0292055 | A1* | 11/2008 | Boone | 378/97 |
| 2011/0202324 | A1 | 8/2011 | Currell et al. | |

FOREIGN PATENT DOCUMENTS

| WO | 2007062178 A2 | 5/2007 |
|---|---|---|
| WO | 2008150511 A2 | 12/2008 |

OTHER PUBLICATIONS

Chu, C-M., et al.; Numerical Solution of Problems in Multiple Scattering of Electromagnetic Radiation; 1955; The Journal of Physical Chemistry; 59(9)855-863. Feb. 1955.

(Continued)

*Primary Examiner* — Stephen R Koziol
*Assistant Examiner* — Amandeep Saini

(57) ABSTRACT

A method of determining a distribution of a dose in a body is presented including the steps of scanning at least one region of the body to extract image data, calculating a plurality of parameters from the image data, and entering a plurality of computed tomography (CT) scan parameters. The method also includes the steps of calculating radiation distribution by using a local interaction principle and creating a three-dimensional dose map based on the calculated radiation distribution.

17 Claims, 4 Drawing Sheets

(56) References Cited

OTHER PUBLICATIONS

Grant, I. P., et al.; Radiative Transfer in a Rayleigh Scattering Atmosphere; 1968; J. Quant. Spectrosc. Radiat. Transfer; vol. 8; pp. 1817-1832. Jun. 1968.

Lovejoy, S., et al.; Multifractals, Universality Classes and Satellite and Radar Measurements of Cloud and Rain Fields; 1990; Journal of Geophysical Research; 95(D3)2021-2034. Feb. 1990.

Transpire, Inc.; Attila Radiation Transport Software http://www.transpireinc.com/html/attila accessed Mar. 12, 2015.

* cited by examiner

METHOD OF DETERMINING DISTRIBUTION OF A DOSE IN A BODY

CROSS REFERENCE TO RELATED APPLICATIONS

This application is a national filing of PCT application Ser. No. PCT/IB2013/059266, filed Oct. 10, 2013, published as WO 2014/060913 A1 on Apr. 24, 2014, which claims the benefit of U.S. provisional application Ser. No. 61/715,930 filed Oct. 19, 2012 and U.S. provisional application Ser. No. 61/716,843 filed Oct. 22, 2012, both of which are incorporated herein by reference.

The present application generally relates to methods for "computed tomography" (CT) and other radiation imaging systems, and more particularly, to a method of determining a local patient dose applied to a patient in computed tomography.

Dose-maps show the distribution of a dose in a body of a patient and an organ dose is a dose absorbed by a specific organ in the body of the patient. Until recently, time and computer resources required for such doses were too large to make them relevant tools in clinical applications.

Dose-maps are usually calculated with Monte-Carlo-Simulations, which are accurate. However, such simulations are slow even on a larger cluster of computers. Therefore, such simulations are not used in hospitals, which do not have such clusters of computers. Also, regarding research and development, such simulations are used only in exceptional cases due to the need of multiple resources.

Besides Monte-Carlo-Simulations, at least one source has developed software code that numerically solves the Boltzmann-Transport-equation for computing dose-maps. This model is faster than Monte-Carlo-Simulations, but still requires more resources and calculation time than a typical hospital has.

Therefore, in the present disclosure, a model based on radiation transfer theory is proposed, which is solved, in an approximate manner, with a local interaction principle. In contrast to the Monte-Carlo-Simulations and the Boltzmann-Transport-equation, the proposed hypothesis cannot be used for questions concerning, e.g., image quality or scattering corrections. However, this model, by using the local interaction principle, is much simpler than the two former ones and may calculate dose maps with accuracy, with less computer resources, and in shorter time periods.

Aspects of the present application address the above-referenced matters and others.

According to one aspect, a method of determining a distribution of a dose in a body includes the steps of scanning at least one region of the body to extract image data, calculating a plurality of parameters from the image data, and entering a plurality of computed tomography (CT) scan parameters. The method also includes the steps of calculating radiation distribution by using a local interaction principle and creating a three-dimensional dose map based on the calculated radiation distribution.

In another aspect, a method of determining a distribution of a dose in a body includes allowing the selection of image data having a plurality of parameters, adjusting one or more of the plurality of parameters selected, and running an algorithm using a local interaction principle. The method also includes the steps of calculating radiation scattering by using the local interaction principle, creating a three-dimensional dose map and displaying the does map on a display unit.

Still further aspects of the present invention will be appreciated to those of ordinary skill in the art upon reading and understanding the following detailed description.

The invention may take form in various components and arrangements of components, and in various steps and arrangements of steps. The drawings are only for purposes of illustrating the preferred embodiments and are not to be construed as limiting the invention.

Figure 1:
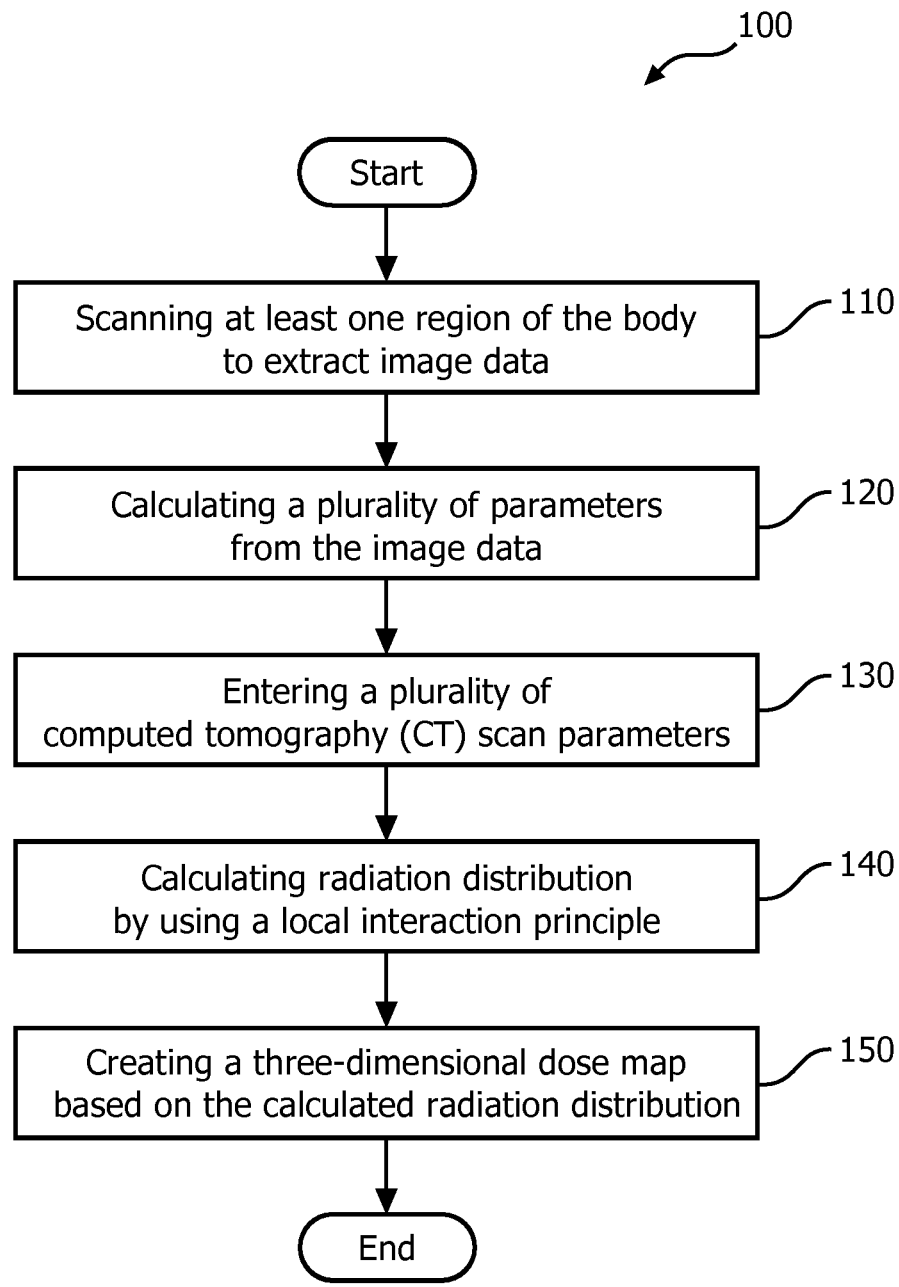
FIG. 1 illustrates an example flowchart of a method for determining a distribution of a dose in a body of a patient.

With reference to FIG. 1, the flowchart 100 illustrates a method for determining a distribution of a dose in a body of a patient. In step 110, scanning at least one region of the body to extract image data is performed. In step 120, a plurality of parameters are calculated from the image data, as described below. In step 130, a plurality of CT scan parameters are entered, as described below. In step 140, radiation distribution is calculated by using a modified or customized local interaction principle. In step 150, a three-dimensional dose map is created based on the calculated radiation distribution. The process then ends for the first iteration.

Therefore, the modified or customized local interaction principle is used to calculate the transfer of x-ray radiation in the human body. The local interaction principle allows for a fast solution of the radiation transfer equation. The exemplary embodiments of the present disclosure propose a method of evaluating dose maps and calculating organ doses based on a variation of the local interaction principle.

The method presented herein aims at improving the speed of calculations of dose maps and organ doses and the requirements of the computer utilized, so that they are useful for clinical usage and for a much wider range of research and development projects. It is possible to calculate dose maps or organ doses with other imaging methods, and after a clinical scan, based on the CT images or to use the CT scan data of a typical person, to optimize a scan in advance, with respect to the dose, by comparing different scan protocols and parameters, as discussed below.

The radiation transfer equation is solved by having the space and the scattering directions of radiation discretized. The term "discretized" refers to the process of transferring continuous models and equations into discrete components. This can be performed in a variety of ways. However, in the exemplary embodiments of the present disclosure, cubic voxels are used for the space and 6 directions are used for the scattering. The formula used to determine the scattering directions of radiation is given as follows:

$$I_{+x}(i, j, k) = \\ T(i, j, k) * I_{+x}(i-1, j, k) + R(i, j, k) * I_{-x}(i+1, j, k) + S(i, j, k) * \\ (I_{+y}(i, j-1, k) + I_{-y}(i, j+1, k) + I_{+z}(i, j, k-1) + I_{-z}(i, j, k+1))$$

Of course, one skilled in the art may contemplate using any type of pixels in any number of scattering directions. Additionally, radiation is scattered equally in all directions. As an input, the model requires the attenuation factors in every voxel in the scanned area. This information is contained in CT pictures. Therefore, standard image data of CT scans are also used as input. Such input is rescaled to precision, i.e., the voxel size, chosen for the dose map. Of course, the rescaling step may be optional. Then the radiation transfer is calculated with the modified or customized local interaction principle and the results may be visualized via a display unit. These steps are illustrated in FIG. 1. In one exemplary embodiment, the CT scan parameters are rotated to increase the accuracy of the approximation used with the modified or customized local interaction principle.

In the exemplary embodiments, the proposed model starts with image data of a real scan as input. For convenience and for higher calculation speed, this data is rescaled so that the data has, for example, a 128*128 or 64*64 voxel grid in the x-y plane instead of the 512*512 voxel grid of usual image data. Also, in the z-direction, the data are rescaled to get cubic voxels because image data usually have a different resolution in the z-direction than in x and y directions. The rescaling of the data and the use of cubic voxels is performed in order to simplify the model and to reach a higher calculation speed. However, it is noted that the rescaling of the data may be optional.

These image data yield the attenuation factors of each voxel of the scanned region. Other parameters of the model that may be used are the phase function for the scattering of the radiation. Because the relevant scattering effects for CT scans, photoelectric-scattering and Compton-scattering, are well known, these parameters can be chosen based on analytic results and data, which are published and openly accessible, or via a look-up table. Other parameters that may be determined via a look-up table are a parameter related to a ratio between photo-electric and Compton scattering and a parameter related to the density of each voxel.

Moreover, other parameters used, that are calculated, are a parameter related to the geometry of the scanner and a parameter related to the profile of the radiation. With these parameters and the modified or customized local interaction principle, the radiation transfer in the body of a patient is calculated. As a result, the absorbed dose or absorbed energy in every voxel may be calculated based on a combination of calculated parameters and/or manually inputted parameters.

The field of absorbed doses or absorbed energy may be visualized in various forms. For example, a two-dimensional plot cuts along the axises through these three-dimensional fields. Additionally one may identify a certain region/assembly of voxels according to the CT number as an organ, e.g., the lung, the heart, the liver, the eyes, or the breast. The absorbed dose averaged over the voxel/region is referred to as the organ dose.

Additionally, the following equations may be used to calculate the absorption of a dose.

$$Abs_{pe} = ((I_{+x}(i-1, j, k) + (I_{-x}(i+1, j, k) +$$
$$(I_{+y}(i, j-1, k) + (I_{-y}(i, j+1, k) + (I_{+z}(i, j, k-1) +$$
$$(I_{-z}(i, j, k+1)) * (1 - \mu(i, j, k)) * ab(i, j, k)$$
$$Abs_{compton} = ((I_{+x}(i-1, j, k) + (I_{-x}(i+1, j, k) +$$
$$(I_{+y}(i, j-1, k) + (I_{-y}(i, j+1, k) +$$
$$(I_{+z}(i, j, k-1) + (I_{-z}(i, j, k+1)) *$$
$$(1 - \mu(i, j, k)) * (1 - ab(i, j, k)) * (1 -$$
$$(T(i, j, k) + R(i, j, k) + 4S(i, j, k)))$$

$$Abs_{total} = Abs_{pe} + Abs_{compton}$$

Where "Abs" is the absorbed energy and the index "pe" means photo-electric and Compton refers to energy absorbed in Compton-scattering.

$$E_{in} = \sum_{j,k} I_{+x}(1, j, k) + I_{-x}(i_{max}, j, k) + \sum_{i,k} I_{+y}(i, 1, k) + I_{-y}(i, j_{max}, k)$$

$$E_{out} = \sum_{j,k} I_{-x}(1, j, k) + I_{+x}(i_{max}, j, k) + \sum_{i,k} I_{-y}(i, 1, k) +$$
$$I_{+y}(i, y_{max}, k) + \sum_{i,j} I_{-z}(i, j, 1) + I_{+z}(i, j, k_{max\square})$$

$$f_{stop} = \frac{E_{in} - E_{out} - Abs_{total}}{E_{in}}$$

Where "mu" is the attenuation factor of the cell times the length of the cell and "ab" is the ratio between photoelectric and Compton-scattering.

"E_in" is the incoming energy, i.e., the x-ray from the source according to the initial conditions.

"E_out" is the energy that leaves the grid on which the calculation is performed.

"f_stop" is the factor according to which a decision is made whether the iterative calculation converged enough already, e.g., the stopping criterion can be f_stop<1% or 0.1% according to the wished for precision of the calculation.

"i," "j," and "k" are unit vectors in the x, y, and z axes, respectively.

"R," represents the backward scattering of the radiation.

"S," represents the scattering of the radiation to the side.

"T," represents the probability of forward-transfer of the radiation, where T can be expressed as:

$$T = 1 - \mu + \mu*F = 1 - \mu*(1-F)$$

Where "F" is the forward scattering probability and "mu" is the attenuation factor of the cell times the length of the cell.

In use or operation, the CT image data are selected or the scan-protocol parameters are selected for a standard image data included in the model. Next, the application is started by clicking on a dedicated icon. A dialog box is opened, where several parameters may be adjusted. A "continue" button may then be clicked. Subsequently, the software reads the selected image data. After running the algorithm, it creates a 3D dose map or a 3D map of absorbed energy. The result may be visualized in various ways. A region may be marked in the resulting map or in the input image data and the organ-dose for this region is received.

Additionally, scan parameters and/or scan protocols may be selected or the scan parameters and/or scan protocols of the actual scan may be used. Besides these parameters, the resolution of the output dose map may be chosen. After such calculation, a region of the map (or of the input image data) may be chosen to calculate the organ dose.

Figure 2:
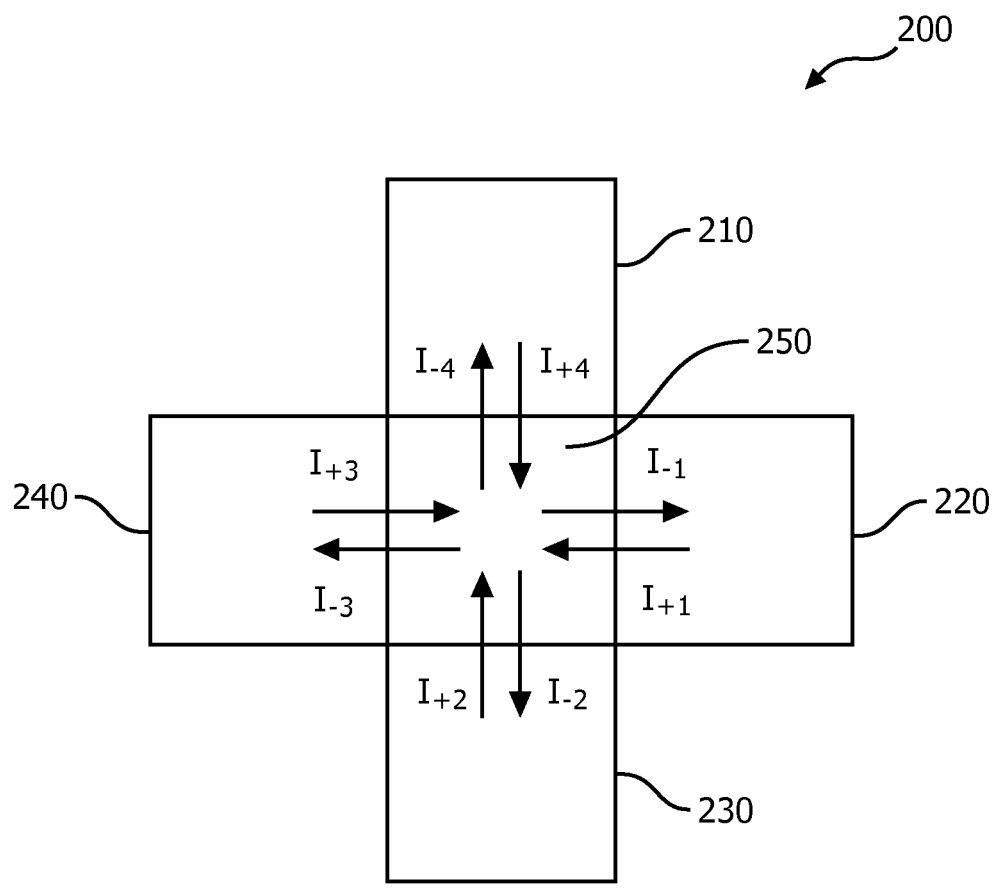
FIG. 2 illustrates an example of applying the local interaction principle to a plurality of voxels.

Therefore, the modified or customized local interaction principle allows the calculation of the radiant flux in each voxel by taking into account the radiant flux from and to the neighboring voxels. This is illustrated for a two-dimensional case in FIG. 2, where a plurality of voxels 200 are depicted. For example the radiant flux, $I_{-1}$, leaving the central voxel may be calculated as follows:

$$I_{-1} = F*I_{+2} + S*(I_{+2} + I_{+2}) + B*I_{+1}$$

In other words, the flux from the central voxel 250 to its right neighbor (i.e., voxel 220) is the sum of the flux that it gets from its left neighbor (i.e., voxel 240) times the forward-scattering-probability F (including the fraction that passes the central voxel 250 without scattering) plus the flux from its upper voxel 210 and its lower voxel 230, times the side-scattering-probability, S, plus the flux from its right neighbor (voxel 220) times the back-scattering-probability, B. The local interaction principle is an accurate first order approximation of the full radiation transfer equation. The local interaction principle may be used, for example, in an iterative way, where each iteration step is similar to a matrix multiplication of a vector, which contains the radiant flux in each voxel and the matrix is composed of the parameters F, S, and B of the equation above.

Figure 3:
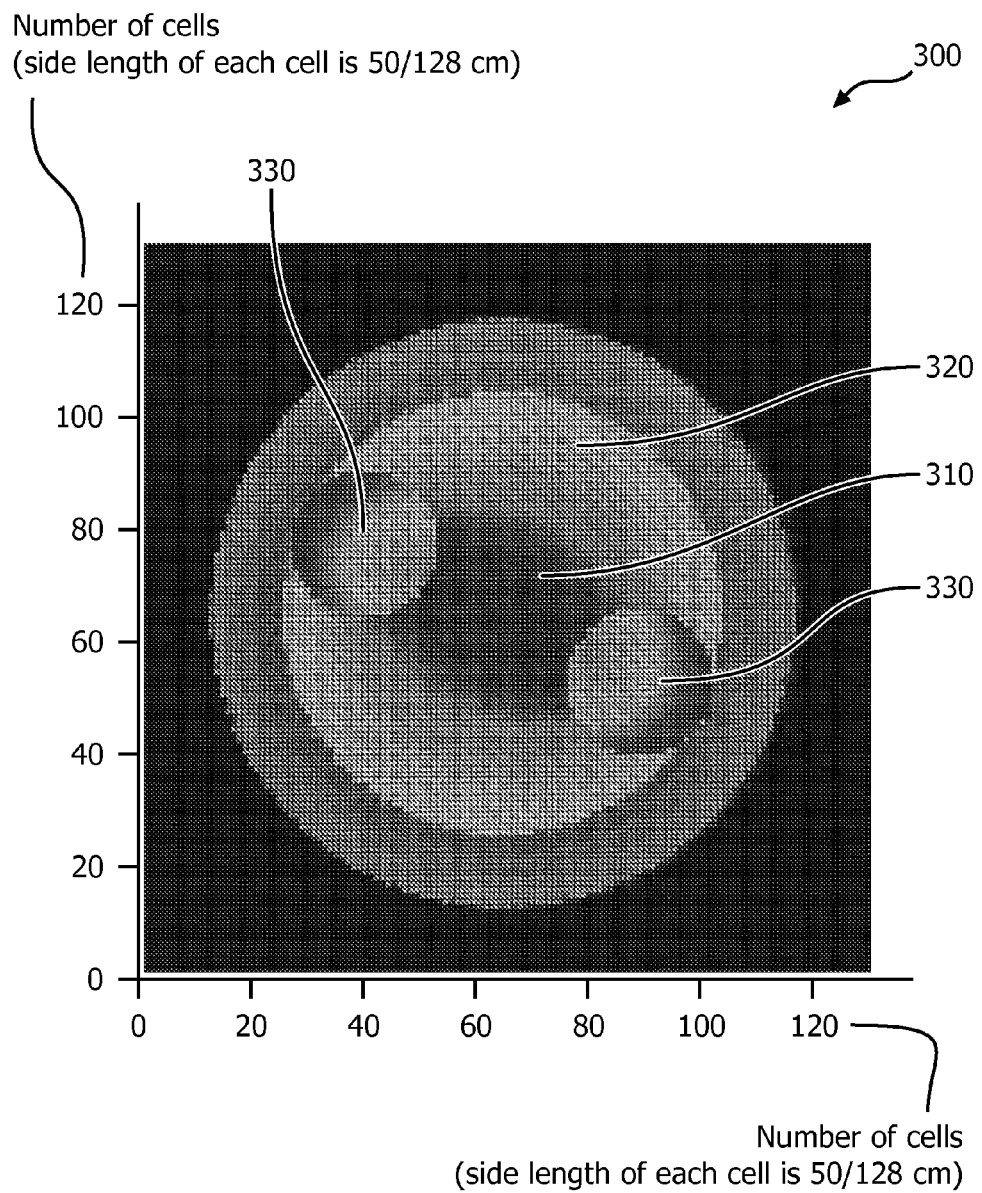
FIG. 3 illustrates an example of a dose map of a body part of the patient.

Referring to FIG. 3, a map 300 illustrating a virtual phantom including four ball shapes is presented. A first ball 320 with a radius of 20 cm and an attenuation factor of fat is centrally shown. A second ball 310 with a radius of 15 cm and an attenuation factor of water is centrally shown within the first ball 320. Two smaller balls 330 with an attenuation of dense bones is also illustrated. Map 300 was calculated with the local interaction principle described herein. The shapes are provided according to a logarithmic scale, the difference between the highest and lowest values depict is a factor of 10. The calculations in FIG. 3 were made with a resolution of 128×128 cells, and the x and y axes show the number of cells, where every cell has a side-length of 50/128 cm.

Figure 4:
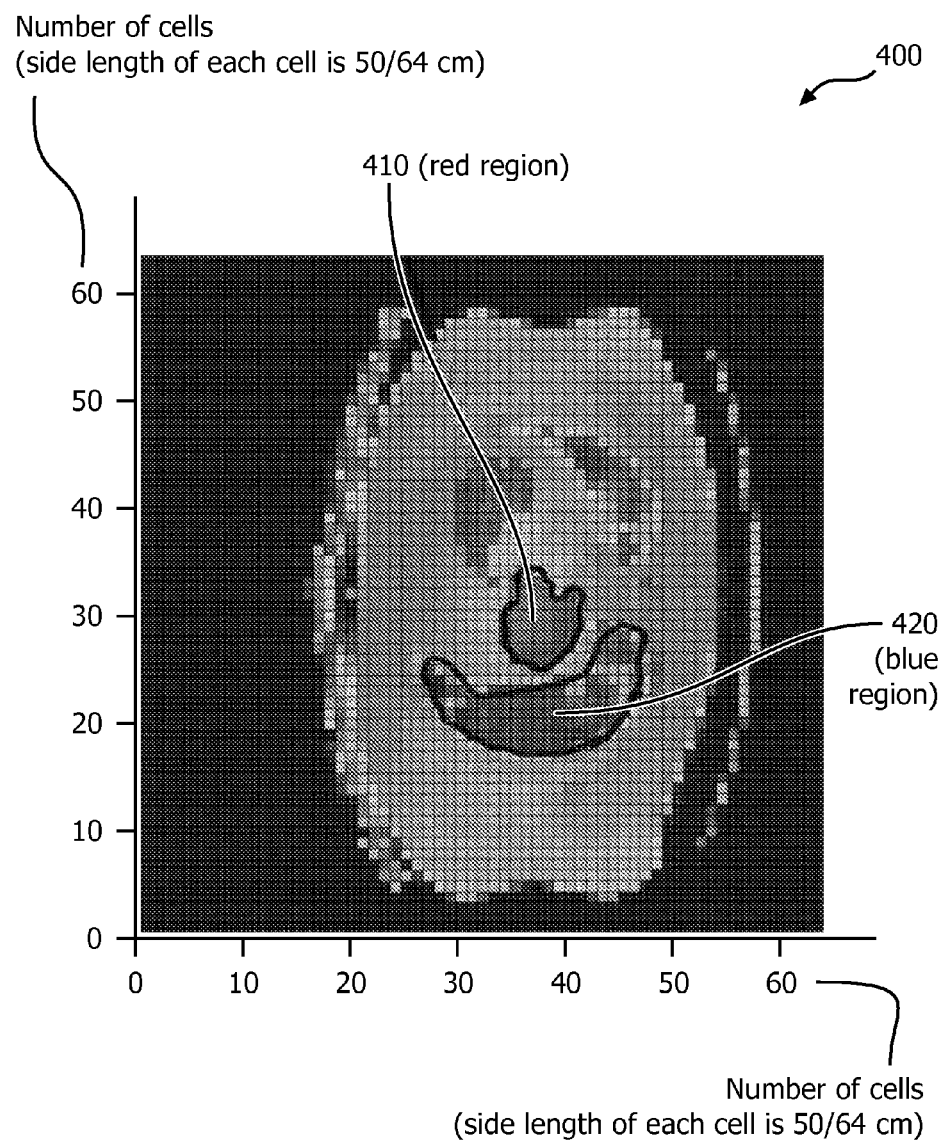
FIG. 4 illustrates an example of a dose map calculated based on a CT scan.

Referring to FIG. 4, a map 400 calculated based on a CT scan is presented. For example, the blue region 420 inside the body indicates the area of the lung with lower absorption and the red region 410 in the middle is the heart. As shown, the heart absorbs lots of radiation due to the iodine of the contrast medium. This map 400 is part of a 64*64*37 voxel field and the calculation using the local interaction principle lasts less than a minute via a computing means (e.g., a personal computer). The calculations in FIG. 4 were made with a resolution of 64×64 cells, and the x and y axes show the number of cells, where every cell has a side-length of 50/64 cm.

Therefore, a modified or customized local interaction principle is applied herein to calculate the transfer of x-rays in human bodies in order to evaluate dose maps and/or the organ dose based on data from CT scans. All local interaction principle model parameters are adjusted to the transfer of x-ray radiation in human bodies.

The proposed method described herein has several advantages over other related documented techniques. In particular, the proposed algorithm is macroscopic in comparison to the standard microscopic Monte-Carlo simulations. Additionally, the proposed algorithm, based on the modified or customized local interaction principle, calculates the radiation transfer similarly to a matrix multiplication, and, is therefore, much simpler than solving the complete Boltzmann-transport-equations. Moreover, the local interaction principle equations allow much faster calculations with less computer power. In other words, calculations are possible in several minutes (or even seconds for small scanned regions with lower precision) on a conventional PC or laptop. This also leads to a noteworthy reduction of cost. Finally, faster and cheaper calculations of dose maps and/or organ doses are possible, thus enabling the use of such tools in hospitals.

It is to be appreciated that the embodiments described above may be used individually or in combination.

The methods described herein may be implemented via one or more processors executing one or more computer readable instructions encoded or embodied on computer readable storage mediums, such as physical memory, which causes the one or more processors to carry out the various acts and/or other functions. The one or more processors can also execute instructions carried by transitory mediums, such as a signal or carrier wave.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A method of determining a radiation distribution of a dose in a body, the method comprising:
   scanning at least one region of the body to extract image data, wherein the image data is represented as a plurality of three-dimensional cubic voxels;
   calculating a plurality of parameters from the image data;
   entering a plurality of computed tomography (CT) scan parameters;
   calculating the radiation distribution by using a customized local interaction principle, which calculates a radiant flux of the plurality of three-dimensional cubic voxels by measuring radiant fluxes flowing between neighboring cubic voxels of the plurality of three-dimensional cubic voxels; and
   creating a three-dimensional dose map based on the calculated radiation distribution.

2. The method according to claim 1, further comprising rescaling the image data.

3. The method according to claim 1, further comprising representing the image data as either a 64×64 voxel grid or a 128×128 voxel grid in an x-y plane.

4. The method according to claim 1, wherein the radiation distribution indicates an energy absorbed in every voxel.

5. The method according to claim 1, wherein the plurality of CT scan parameters includes at least one of attenuation factors, phase function factors, and scattering factors.

6. The method according to claim 1, further comprising computing the radiation distribution in six directions for scattering according to the following formula:

$$I_{+x}(i, j, k) = \\ T(i, j, k) * I_{+x}(i-1, j, k) + R(i, j, k) * I_{-x}(i+1, j, k) + S(i, j, k) * \\ (I_{+y}(i, j-1, k) + I_{-y}(i, j+1, k) + I_{+z}(i, j, k-1) + I_{-z}(i, j, k+1))$$

where 1 represents radiant flux, i, j and k are unit vectors in the x, y, and z axes, respectively, T represents a probability of forward-transfer of the radiation, R represents a backward scattering of the radiation, and S represents a scattering of the radiation to a side.

7. The method according to claim 1, further comprising solving radiation transfer equations, via the customized local interaction principle, by discretizing space and scattering directions of radiation according to the following formula:

$$I_{+x}(i, j, k) = \\ T(i, j, k) * I_{+x}(i-1, j, k) + R(i, j, k) * I_{-x}(i+1, j, k) + S(i, j, k) * \\ (I_{+y}(i, j-1, k) + I_{-y}(i, j+1, k) + I_{+z}(i, j, k-1) + I_{-z}(i, j, k+1))$$

where l represents radiant flux, i, j and k are unit vectors in the x, y, and z axes, respectively, T represents a probability of forward-transfer of the radiation, R represents a backward scattering of the radiation, and S represents a scattering of the radiation to a side.

8. The method according to claim 1, further comprising displaying the dose map on a display unit.

9. The method according to claim 1, further comprising determining the distribution of the dose via positron emission tomography (CT/PET) or single-photon emission computed tomography (CT/SPECT).

10. The method according to claim 1, further comprising rotating the plurality of CT scan parameters for adjusting approximation accuracy.

11. A method of determining a radiation distribution of a dose in a body, the method comprising:
    selecting image data having a plurality of parameters, wherein the image data is represented as a plurality of three-dimensional cubic voxels;
    adjusting one or more of the plurality of parameters selected;
    running an algorithm using a customized local interaction principle;
    calculating the radiation scattering by using the customized local interaction principle, which calculates a radiant flux of the plurality of three-dimensional cubic voxels by measuring radiant fluxes flowing between neighboring cubic voxels of the plurality of three-dimensional cubic voxels;
    creating a three-dimensional dose map; and
    displaying the does map on a display unit.

12. The method according to claim 11, further comprising representing the image data as either a 64×64 voxel grid or a 128×128 voxel grid in an x-y plane.

13. The method according to claim 11, wherein the plurality of parameters includes at least one of attenuation factors, phase function factors, and scattering factors.

14. The method according to claim 11, further comprising computing the radiation scattering in six directions according to the following formula:

$$I_{+x}(i, j, k) = T(i, j, k) * I_{+x}(i-1, j, k) + R(i, j, k) * I_{-x}(i+1, j, k) + S(i, j, k) * (I_{+y}(i, j-1, k) + I_{-y}(i, j+1, k) + I_{+z}(i, j, k-1) + I_{-z}(i, j, k+1))$$

where l represents radiant flux, i, j and k are unit vectors in the x, y, and z axes, respectively, T represents a probability of forward-transfer of the radiation, R represents a backward scattering of the radiation, and S represents a scattering of the radiation to a side.

15. The method according to claim 11, further comprising determining the distribution of the dose via positron emission tomography (CT/PET) or single-photon emission computed tomography (CT/SPECT).

16. The method according to claim 11, further comprising rotating the plurality of parameters for adjusting approximation accuracy.

17. A non-transitory computer readable medium with computer executable instructions encoded thereon which when executed by a processor cause the processor to:
    calculate a plurality of parameters from image data of a scanned subject represented as a plurality of three-dimensional cubic voxels;
    receive a plurality of computed tomography scan parameters;
    calculate a radiation distribution with a customized local interaction principle by calculating a radiant flux of the plurality of three-dimensional cubic voxels by measuring radiant fluxes flowing between neighboring cubic voxels of the plurality of three-dimensional cubic voxels; and
    create a three-dimensional dose map based on the calculated radiation distribution.

* * * * *